US011083693B1

(12) United States Patent
Huang et al.

(10) Patent No.: US 11,083,693 B1
(45) Date of Patent: Aug. 10, 2021

(54) LIPOSOME FORMULATION OF VILANTEROL TRIFENATATE

(71) Applicants: Cai Gu Huang, Shrewsbury, MA (US); Xiao Ting Huang, Shanghai (CN)

(72) Inventors: Cai Gu Huang, Shrewsbury, MA (US); Xiao Ting Huang, Shanghai (CN)

( * ) Notice: Subject to any disclaimer, the term of this patent is extended or adjusted under 35 U.S.C. 154(b) by 0 days.

(21) Appl. No.: 17/151,790

(22) Filed: Jan. 19, 2021

Related U.S. Application Data (60) Provisional application No. 62/963,531, filed on Jan. 20, 2020.

(51) Int. Cl.
*A61K 9/127* (2006.01)
*A61K 31/138* (2006.01)

(52) U.S. Cl.
CPC .......... *A61K 9/1277* (2013.01); *A61K 31/138* (2013.01)

(58) Field of Classification Search
CPC .................................................... A61K 31/138
See application file for complete search history.

(56) References Cited

U.S. PATENT DOCUMENTS 6,007,838 A * 12/1999 Alving ................ A61K 9/1277 264/4.1
2004/0071770 A1 4/2004 Smith
2013/0319411 A1 12/2013 Weers et al.

FOREIGN PATENT DOCUMENTS

WO 03/024439 * 3/2003
WO 2003024439 A1 3/2003
WO 2018178264 A1 10/2018
WO 2019011998 A1 1/2019

OTHER PUBLICATIONS

International Search Report and Written Opinion issued in PCT/US2021/013866, filed Jan. 19, 2021 and from the ISA/US dated Jun. 2, 2021.

* cited by examiner

*Primary Examiner* — Carlos A Azpuru
(74) *Attorney, Agent, or Firm* — Parker Poe Adams & Bernstein

(57) ABSTRACT

The present invention is directed to a liposomal formulation comprising a lipid ingredient encapsulating vilanterol trifenatate, and a method for administering the liposomal formulation by nebulizing the liposomal formulation in an inhaler. The liposomal formulation comprises vilanterol or a salt thereof, and lipid ingredients comprising a pharmaceutical lipid and/or a sterol. The drug to lipid mass ratio is in the range of about 1:20 to about 1:100. Additionally, the present invention is directed to the use of the liposomal formulation for the prevention or treatment of respiratory diseases such as Chronic Obstructive Pulmonary Disease and/or asthma.

12 Claims, 9 Drawing Sheets

LIPOSOME FORMULATION OF VILANTEROL TRIFENATATE

PRIORITY STATEMENT

This application claims the benefit of the filing date of U.S. Provisional Patent Application No. 62/963,531, filed on Jan. 20, 2020, the contents of which are incorporated herein by reference in its entirety.

FIELD OF THE INVENTION

The present invention relates to a liposome formulation and a preparation method for the liposome formulation.

BACKGROUND OF THE INVENTION

Vilanterol trifenatate, chemically known as 4-{(1R)-2-[(6-(2-((2,6-dichlorobenzyl) oxy) ethoxy) hexyl) amino]-1-hydroxyethyl}-2-(hydroxymethyl) phenol mono (2,2,2-triphenylacetate) has been described in WO03/024439. Vilanterol trifenatate has the following chemical structure:

Vilanterol trifenatate has been described as a long-acting muscarinic antagonist that activates beta-2 adrenoreceptors on airway smooth muscle, causing broncho-dilation. Beta-2 receptors are the adrenergic receptors in bronchial smooth muscle. Vilanterol trifenatate can provide a therapeutic benefit in the treatment of asthma or chronic obstructive pulmonary disease (COPD), including chronic bronchitis and emphysema.

Vilanterol trifenatate has been administered by means of dry powder inhalation. However, administration by dry powder inhalation is difficult or unpleasant for some patients, in particular for children and the elderly. As an aspect of the present invention, to increase the delivery of vilanterol trifenatate to the desired targets and reduce the incidence of side effects associated with it, vilanterol trifenatate is encapsulated in a lipid bilayer to make it available only at the site of action while minimizing the effect on other tissues.

Liposomes are microscopic closed vesicles which have an internal phase enclosed by one or more lipid bilayers. Liposomes can entrap an active agent. Vilanterol trifenatate can be entrapped in liposomes with high efficiency, wherein the vilanterol trifenatate is retained in liposome constituents so that the vilanterol trifenatate can be delivered to a target tissue. Liposomes can improve protection of an encapsulated drug, increase drug stability, change the in vivo distribution behavior of the drug, and carry the drug to a diseased region by passive or active targeting, as well as improve drug efficiency and reduce drug toxicity.

Accordingly, the present invention relates to liposomal formulations, which are particularly suitable for administering vilanterol trifenatate by nebulization inhalation, and which are especially suitable for the treatment of asthma and chronic obstructive pulmonary disease.

Moreover, the present invention relates to liposomal formulations having particle size uniformity, high drug-loaded capacity as well as high encapsulation efficiency. The liposomal formulations disclosed in the present invention are suitable for administration by nebulization inhalation.

Furthermore, administration of a liposomal formulation by inhalation is advantageous compared to administration by conventional dry powder inhalation. For example, administration by dry powder inhalation is more difficult, particularly for children and elderly patients. Also, dry powder inhalation may cause side effects on the lung. The liposomal formulations of the present invention are particularly suited for administering vilanterol trifenatate by nebulization inhalation, especially for treating asthma and chronic obstructive pulmonary disease.

It is now surprisingly found that a novel liposomal formulation of vilanterol trifenatate can be prepared and that this liposomal formulation is very stable and suitable for nebulization inhalation.

SUMMARY OF THE INVENTION

Aspects and advantages of the current invention will be set forth in part in the following description, or may be obvious from the description, or may be learned through practice of the invention.

The present invention relates to formulations comprising vilanterol trifenatate encapsulated in liposomes and methods for their preparation. One aspect of the present invention provides liposomes having a high uniformity, which results in minimizing side effects, high drug-loading capacity, high encapsulation efficiency, and good stability, which are suitable for administration by nebulization inhalation.

The liposomal formulation is characterized by liposomes having desirable compositions and physical characteristics. The liposomal formulations of the present invention comprise one or more lipid ingredient encapsulating vilanterol trifenatate.

The liposome formulations of the present invention comprise liposomes comprising one or more lipid ingredients and vilanterol trifenatate, wherein the mass ratio of the vilanterol trifenatate to that of the lipid ingredient(s), called the drug to lipid ratio, is in the range of about 1:10 to about 1:150 by weight, such as about 1:10 to about 1:50 by weight. This drug to lipid ratio enhances stability and effectiveness of liposome and also has an impact on drug release and liposome integrity. These and other structural characteristics impart unexpected benefits to the instant formulation.

The liposomes of the present invention have a size in the range from about 50 to about 500 nm, more preferably in the size range of about 100 to about 400 nm, depending on the type of vilanterol trifenatate and/or the direct carrier used. In one embodiment, the liposomes are in the size range of about 150 to about 170 nm.

Another aspect of the present invention is to provide two preparation methods, preparation method 1 and preparation method 2, for preparing liposome formulations. Liposomes formulated by these process have desirable characteristics. Preparation method 1 for preparing the liposomes includes: (1) preparation of vilanterol trifenatate solution, (2) mixing the as-prepared vilanterol trifenatate solution with a lipid and a sterol to provide a mixture, and (3) extruding the mixture. Preparation method 2 for the preparing the liposomes includes: (1) preparing a drug solution, (2) injecting a solution containing lipid ingredients into the drug solution to provide a mixture, and (3) adjusting the pH of the resulting mixture. Each of these methods produces a solution containing liposome vesicles comprising a drug, such as vilanterol trifenatate.

If desired, a further step of ultrafiltration and concentration of the resulting liposome vesicle-containing solution may be included in the preparation processes.

The preparation methods of the current invention are suitable for commercial production by scaling up preparation of a liposomal formulation of vilanterol trifenatate.

In one embodiment, a formulation is prepared by (1) preparing a drug solution; (2) injecting into the drug solution a lipid solution made from lipid ingredients comprising DPPC, DSPG, and cholesterol in a molar ratio of about 1:5:1 to about 1:10:6, more particularly about 1:9:5, and wherein the mass ratio of vilanterol trifenatate to lipid is in the range of about 1:10 to 1:150; (3) adding water to the desired volume; and (4) adjusting the pH of the resulting solution.

Yet another aspect of the present invention is a liposomal formulation made in accordance with the methods described above. The formulation comprises a plurality of liposomes, composed of an amount of one or more lipid ingredients encapsulating vilanterol trifenatate. In one embodiment, the lipid ingredients comprise one or more of DPPC, DSPG, and cholesterol, and the mass ratio of vilanterol trifenatate to lipid ingredient(s) is in the range of about 1:10 to about 1:150. In an embodiment, the formulation is prepared by: (1) preparing a vilanterol trifenatate solution, (2) preparing a lipid and cholesterol solution, (3) mixing the vilanterol trifenatate solution with the lipid and cholesterol solution to provide a mixture, and (4) extruding the mixture.

The above described methods can produce a liposomal formulation, which has useful characteristics, by, for example, varying the ratio of the lipid ingredient(s), the drug to lipid ratio, and the pH value, so as to be suitable for administration by nebulization inhalation or soft mist inhalation.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

DETAILED DESCRIPTION OF THE INVENTION

For purposes of the describing the invention, reference now will be made in detail to embodiments and/or methods of the invention, one or more examples of which are illustrated in or with the drawings. Each example is provided by way of explanation of the invention, not limitation of the invention. In fact, it will be apparent to those skilled in the art that various modifications and variations can be made in the present invention without departing from the scope or spirit of the invention. For instance, features or steps illustrated or described as part of one embodiment can be used with another embodiment or steps to yield still further embodiments or methods. Thus, it is intended that the present invention covers such modifications and variations as come within the scope of the appended claims and their equivalents.

The present invention relates to a liposomal formulation and two methods for preparing the liposomal formulation. The formulation comprises a plurality of liposomes encapsulating vilanterol trifenatate. The physical characteristics of each liposome facilitate stability and effectiveness of the liposomal formulation. The formulation is characterized by liposomes which are substantially uniform in size and shape distribution.

Additionally, the invention provides an efficient method for preparing the liposomal formulation, which can meet the needs of large-scale preparation.

As used herein, the term "liposome" refers to microscopic closed vesicles having an internal phase enclosed by a lipid bilayer. In the present invention, liposome includes, but is not limited to, small single-membrane liposome, large single-membrane liposome, still larger single-membrane liposome, multilayer liposome having multiple concentric membranes, liposome having multiple membranes that are not concentric, but irregular.

The term "liposome internal phase" refers to an aqueous region enclosed in the lipid bilayer of the liposome, and has the same meaning as "internal water phase" and "liposome internal water phase."

The present invention relates to a liposomal formulation. Different liposome ingredients may be used to form the liposomes of the invention. In an embodiment, the lipid ingredient comprises one or more non-toxic biocompatible lipids, for example, lipids prepared from phosphatidylcholine, phosphoglycerol, and/or cholesterol. In one embodiment, the lipid ingredient comprises dipalmitoylphosphatidylcholine (DPPC), diastearoylphosphatidylcholine (DSPC), diastearoylphosphatidylglycerol (DSPG) and cholesterol, or combinations thereof, In another embodiment, the lipid ingredient comprises DPPC, DSPG, and cholesterol, which may be present in a molar ratio of about 9:1:5 (DPPC:DSPG:cholesterol).

As used herein, the term "lipid ingredients" refers to one or more sterols and/or one or more lipids. Exemplary lipid ingredients include, for example, but are not limited to, cholesterol and diastearoylphosphatidylglycerol (DSPG), cholesterol and dipalmitoylphosphatidylcholine (DPPC).

The liposome is not particularly limited in terms of form as long as it is a liposome capable of encapsulating a drug.

The term "encapsulating" means taking a form in which a drug is contained in an inner water phase enclosed by the liposome membrane. For example, the liposome may be a form where drug is encapsulated within a closed space formed of a membrane, a form where a drug is included in the membrane itself, or a combination thereof.

As used herein, the term "average particle size" refers to an average value of diameters of liposomes as measured by a light scattering method.

The liposome is preferably in the form of spherical shape or a morphology close thereto.

The term "step" as used herein includes not only an independent step, but also a step which may not be clearly separated from another step, insofar as an expected outcome of the step can be attained.

The liposomal formulation is characterized by liposomes having a desirable composition and physical characteristics. The liposomes of the present invention comprise lipid ingredients encapsulating vilanterol trifenatate. In an embodiment, the lipid is selected from the group consisting of phosphatidylcholine (PC), phosphatidic acid (PA), phosphatidylethanolamine (PE), phosphatidylglycerol (PG), phosphatidylserine (PS), phosphatidylinositol (PI), dimyristoyl phosphatidyl choline (DMPC), distearoylphosphatidyl choline (DSPC), dipalmitoyl phosphatidyl choline (DPPC), dimyristoyl phosphatidyl glycerol (DMPG), distearoylphosphatidyl glycerol (DSPG), dioleoyl phosphatidyl glycerol (DOPG), dipalmitoylphosphatidylglycerol (DPPG), dimyristoyl phosphatidyl serine (DMPS), distearoyl phosphatidyl serine (DSPS), dioleoyl phosphatidyl serine (DOPS), dipalmitoyl phosphatidyl serine (DPPS), dioleoyl phosphatidyl ethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyp-cyclohexane-1-carboxylate (DOPE-mal), dipalmitoyl phosphatidyl ethanolamine (DPPE), dimyristoylphosphoethanolamine (DMPE), distearoyl-phosphatidylethanolamine (DSPE), di stearoylphosphatidylcholine (DSPC), dioleoylphosphatidylcholine (DOPC), dipalmitoylphosphatidylcholine (DPPC), palmitoyloleoylphosphatidylcholine (POPC), and palmitoyloleoyl-phosphatidylethanolamine (POPE).

In an embodiment, the sterol is selected from the group consisting of cholesterol, ergosterol, and lanosterol, and combinations thereof.

The phrase "drug to lipid ratio" as used herein refers to the relative amounts of the drug to the lipid ingredient(s) by mass. In one embodiment, the liposome has a drug to lipid ratio in the range of about 1:10 to about 1:150 by weight. In another embodiment, the liposome has a drug to lipid ratio in the range of about 1:20 to 1:100 by weight.

The pH affects the properties of the liposomal formulation. The pH affects the stability, drug leakage rate from the liposome, and drug encapsulation capability of the liposomal formulation.

In an embodiment, the liposomal formulation comprises a plurality of liposomes which have the characteristics described above and are substantially uniform in size and shape. The liposomes may be in the size range of about 50 to about 500 nm. In an embodiment, the size range is about 100 to about 400 nm.

In another embodiment, the size range is about 100 to about 300 nm. In a particular embodiment, the size of the liposome is about 110 to about 140 nm.

In another particular embodiment, the size of the liposome is about 150 to about 170 nm.

In one embodiment, the liposomal formulation is formulated using one or more physiologically acceptable carriers comprising excipients and auxiliaries known in the art.

The liposomal formulation may be administered by any route which effectively transports the liposomes to the appropriate site of action. One effective route of administration is inhalation. Other suitable routes of administration include, but are not limited to injection, such as, for example, intramuscular, subcutaneous, or intra-peritoneal injection.

In an embodiment, the liposome formulation comprises an antioxidant selected from the group consisting of water-soluble antioxidants and oil-soluble antioxidants. Examples of oil-soluble antioxidants include, but are not limited to, alpha-tocopherol, alpha-tocopherol succinate, alpha-tocopherol acetate, and mixtures thereof. Examples of water-soluble antioxidants include, but are not limited to, ascorbic acid, sodium bisulfite, sodium sulfite, sodium pyrosulfite, L-cysteine, and mixtures thereof. The amount of the antioxidant added ranges from about 0 to about 1.0% (w/v) of the formulation. In one embodiment, the antioxidant is omitted entirely.

The processes for making the liposomes and liposomal formulations permit manipulation of the physical characteristics described above, as well as allow control of certain process parameters, for example, solvent composition, solvent ratios, and vesicle preparation temperature. Preparation method 1 for the liposomal formulation comprises: (1) preparing a vilanterol trifenatate solution, (2) preparing a lipid solution, (3) mixing the vilanterol trifenatate solution with the lipid solution to provide a mixture, and (4) extruding the mixture. Preparation method 2 for the liposomal formulation comprises: (1) preparing a drug solution, (2) injecting a lipid solution into the drug solution to provide a mixture, (3) adjusting the pH of the mixture.

If desired, a further step of ultrafiltering and concentrating the resulting liposome vesicle-containing solution may be used.

The preparation methods have the advantage of allowing control and monitoring of the physiological and chemical features of the liposomes. For example, the drug to lipid ratio may be managed by selection of the lipid ingredients used to form the liposome or the amount of lipids added to the dissolved active agent. Increasing the amount of lipid ingredient decreases the drug to lipid ratio, and vice versa.

The first two steps of method 1 comprise preparing a vilanterol trifenatate solution and a lipid solution separately. In an embodiment, the ratio of vilanterol trifenatate to solvent is between about 1:5 to about 1:10 (w/v). In an embodiment, DPPC and DSPG, are dissolved in chloroform and methanol in a ratio of about 5:1 to about 10:1 (v/v).

The third step of method 1 comprises mixing the vilanterol trifenatate solution with the lipid solution.

The fourth step of method 1 involves extruding the mixture. In an embodiment, the extruder is a heated stainless steel extruder at a temperature in the range of about 60° C. to about 70° C. In one embodiment, the extrusion process requires about 5 to about 15 passes to achieve the desired liposome particle size, for example, a vesicle size in the range from about 80 nm to about 500 nm.

The process of extrusion reduces the size of the multilamellar vesicles. The method uses a single extrusion step, and low pressure to produce liposomes that are highly-uniform in size and shape.

Extrusion of liposomes using a polycarbonate membrane is an effective method for reducing the size of the liposomes to a relatively well-defined size distribution. In one embodiment, the extruder temperature is above the lipid transient-phase temperature, so as to enable size reduction. For example, in the case of DPPC, DSPG, and cholesterol, a temperature in the range of about 60° C. to about 70° C. may be suitable. Other lipids may be used and their known transient-phase temperature determines the desired temperature for the extrusion step. Multiple passes may be required to achieve the desired vesicle size and homogeneity.

In one embodiment, the extrusion process requires about 9 to about 11 passes to achieve liposome vesicles of in the size range of about 120 nm to about 270 nm.

The first step of method 2 involves preparing a drug solution. In an embodiment, vilanterol trifenatate is dissolved in NaCl solution.

In an embodiment, a lipid solution is prepared by dissolving lipid ingredient(s) at a temperature in the range of about 40° C. to about 80° C. The second step involves injecting the lipid solution into the drug solution, and the third step, is to make the final volume and pH adjustment.

If desired, a step of ultrafiltration and concentration may be conducted. Different types of filtration membranes may be used during the ultrafiltration process. In one embodiment, the ultrafiltration step uses a hollow fiber membrane, where the formulation is pushed through the open hollow cores of the fiber while the relatively larger liposomes remain within the fiber.

In one embodiment, when a hollow fiber cartridge is used for ultrafiltration, the cartridge is filled with 100% alcohol for about 40 minutes to about 80 minutes. In an embodiment, the cartridge is soaked for over one hour. In an embodiment, the alcohol is pumped through the cartridge at about 3 to about 8 psi. In an embodiment, the alcohol is removed, and the cartridge is rinsed with clean water.

In an embodiment, a reused hollow fiber cartridge is used. In such an embodiment, before ultrafiltration, the fiber cartridge may be washed with pure water, and then the sample may be pumped through the cartridge for ultrafiltration, until the liposome sample is concentrated to a desired concentration. After finishing ultrafiltration, the cartridge may be washed by pure water, and then the cartridge may be soaked with about 3% to about 10% NaOH solution.

In an embodiment, the ultrafiltration and concentration may be accomplished using a peristaltic pump connected with a hollow fiber cartridge. In such embodiment, before ultrafiltration, the fiber cartridge may be washed by pure water, and then the sample of liposome formulation may be pumped through the cartridge for ultrafiltration, until the sample is concentrated.

In an embodiment, the liposome formulation may be filtered by a hollow fiber cartridge for concentrating to a volume of, for example, about 10 mL and removing ethanol and free vilanterol trifenatate.

In an embodiment, after ultrafiltration, the hollow fiber cartridge may be washed by pure water, and then soaked with 5% NaOH.

After ultrafiltration, the process may further include a dialyzing step wherein the formulation is dialyzed against a volume of buffered solution. In one embodiment, the buffer solution is normal saline. Other buffer additives are known in the art, including, but not limited to, sucrose, glycine, sodium and/or succinate. In an embodiment, the buffer solution reflects the environment of the final formulation that is external to the liposomes. In an embodiment, the buffer solution is isotonic and non-toxic to cells. The buffer solution may be filtered to further reduce contaminants and may be prepared in advance of the preparation process.

The lipid ingredients may be in the form of a solution containing the desired starting amount of the lipid ingredient(s) in a volume of one or more lipid solvents. Any suitable lipid ingredient(s) and lipid solvent may be used. For example, the lipid ingredients may comprise DPPC and cholesterol in a molar ratio ranging from about 1:3 to about 1:8 prior to liposome formation. The resultant liposome formed according to this combination of lipids may also have about a 1:5 molar ratio of DPPC and cholesterol.

Examples of lipid solvents include, but are not limited to, ethanol, t-butanol, water, and mixtures thereof. In an embodiment, the lipid ingredients are dissolved in the lipid solvent. The lipid solvent may be heated to a temperature that facilitates solubilization of the lipid ingredients, for example, ranging from about 40° C. to about 80° C. to generate the lipid solution.

In an embodiment, the initial concentration of lipid ingredients dissolved in the ethanol is in the range of about 0.20 g/L to about 1.3 g/L. The lipid solution may be prepared apart from the manufacturing process discussed herein.

The liposomal formulation of the present invention may comprise a pH adjusting agent, such as a pharmacologically acceptable base or a pharmacologically acceptable acid.

Pharmacologically acceptable bases include, but are not limited to, alkali metal hydroxides and alkali metal carbonates. In an embodiment, the alkali metal ion is sodium. If bases of this kind are used, it should be ensured that the resulting salts, which are then present in the finished pharmaceutical formulation, are pharmacologically compatible with the above mentioned acid. In one embodiment, the pH adjusting agent is sodium hydroxide.

In an embodiment, the pH of the liposomal formulation prepared according to preparation method 1 is between about 4.0 and about 7.5, such as between about 5.0 and about 7.5.

In one embodiment, the pH of the formulation is adjusted with a pH adjusting agent to a pH between about 6.5 and about 7.0.

In another embodiment, the pH adjusting agent is a pharmaceutically acceptable acid, such as for example, hydrochloric acid, citric acid, ascorbic acid, or a combination thereof.

In one embodiment, the pH adjusting agent is hydrochloric acid.

In an embodiment, the pH of the liposomal formulation prepared according to preparation method 2 is between about 1.0 and about 4.0, such as between about 1.0 and about 3.0, or more specifically about 2.0.

In an embodiment, the drug to lipid ratio in the liposomal formulation may be controlled by varying the amounts of lipid ingredients and vilanterol trifenatate. Optionally, mildly heating the lipid solution or the mixture resulting from combining the drug solution with the lipid solution may aid in mixing together the lipid ingredients and vilanterol trifenatate. This mixing process can result in efficient encapsulation of vilanterol trifenatate into multilamellar vesicles.

The present invention will be described in further detail with reference to the following examples. The following examples are intended to illustrate and exemplify the various aspects of carrying out the present invention and are not intended to limit the scope of the present invention in any way.

EXAMPLES

Materials and Reagents:
Vilanterol trifenatate is commercially available and may be purchased from Shengde Pharmaceutical Co., Ltd.
Dipalmitoylphosphatidylcholine (DPPC) is commercially available and may be purchased from AVT Pharmaceutical Technology Co., Ltd.
Distearoyl phosphatidylglycerol (DSPG) is commercially available and may be purchased from AVT Pharmaceutical Technology Co., Ltd.
Similarly, cholesterol is commercially available and may be purchased from AVT Pharmaceutical Technology Co., Ltd.

Example 1

Preparation Method 1:
Preparation of vilanterol trifenatate solution: NaCl (0.9 g) was added to a beaker containing 100 ml purified water. To this NaCl solution, 117 µL of hydrochloric acid was added. Vilanterol trifenatate (7.03 mg) was added to 70 ml of the solution, then sonicated for 10 min to dissolve. Then, the solution containing vilanterol trifenatate was filtered using a 0.22 µm-filter membrane.
Mixing vilanterol trifenatate solution with lipid solution: DPPC (44.57 mg), DSPG (5.49 mg), and cholesterol (13.20 mg) were combined in a 50-ml round-bottom flask followed by the addition of 18 ml of chloroform and 2 ml of methanol to dissolve the DPPC and DSPG with gentle shaking. The solvent was removed using a rotary evaporator at 65° C., until a thin film of dried lipid was deposited on the walls of the flask. Finally, 20 ml of the prepared vilanterol trifenatate solution was added to the round-bottom flask containing the thin layer of dried lipid. The temperature was maintained at 65° C. for approximately 30 minutes.

Extrusion: The formulation was subjected to extrusion using a heated stainless steel extruder assembled with one polycarbonate membrane at 65° C., to reduce the size of the liposomes and improve homogeneity. The extrusion process was repeated for 9-11 passes to achieve 80-200 nm liposomes. After extrusion, NaOH was added to the liposomal solution to adjust the pH to 6.5-7.0. Finally, the liposomal solution was filtered using a 1-µm GF membrane to obtain liposomes encapsulating vilanterol trifenatate.

Example 2

In accordance with the preparation method described above, four different samples were prepared with high encapsulation efficiency and different drug to lipid ratios. The encapsulation efficiency of each of the four samples was over 97%, and the encapsulation efficiency of each of sample 2 and sample 4 was 100%. The average particle sizes of the liposomes were in the range of about 120 nm to about 320 nm.

Figure 1:
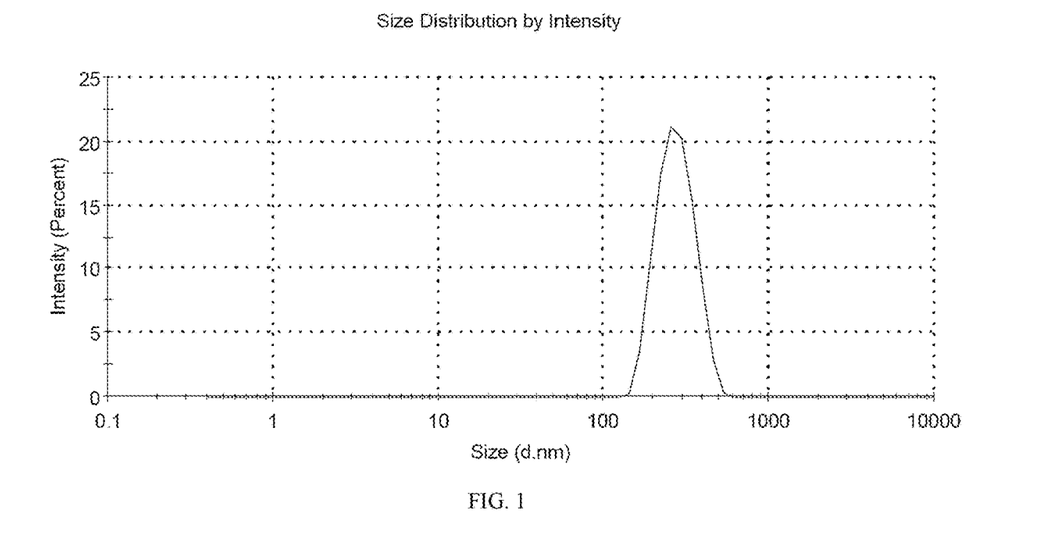
FIG. 1 is a graph of the size distribution of the vilanterol trifenatate liposomes of sample 1 prepared as described in example 2.

Sample 1: NaCl (0.9 g) was added to a beaker containing 100 ml purified water. To this NaCl solution, 117 µL of hydrochloric acid was added. Vilanterol trifenatate (7.03 mg) was added to 70 ml of the solution, then sonicated for 10 min to dissolve. Then, the solution containing vilanterol trifenatate was filtered using a 0.22-µm filter membrane. Then DPPC (178.95 mg), DSPG (21.78 mg), and cholesterol (52.90 mg) were combined in a 50-ml round-bottom flask, followed by addition of 18 ml of chloroform and 2 ml of methanol to dissolve the DPPC and DSPG with gentle shaking. The solvent was removed using a rotary evaporator at 65° C., until a thin film of dried lipid was deposited on the walls of the flask. 20 ml of the prepared vilanterol trifenatate solution was added to the round-bottom flask containing the thin layer of dried lipid. The temperature was maintained at 65° C. for approximately half hour. The formulation was then subjected to extrusion using a heated stainless steel extruder assembled with one polycarbonate membrane at 65° C., to reduce the size of the liposomes and improve homogeneity. The extrusion process was repeated for 9-11 passes to achieve 80-200 nm liposomes. After extrusion, NaOH was added to the liposomal solution to adjust the pH to 6.5-7.0. Finally, the liposomal solution was filtered using a 1-µm GF membrane to obtain liposomes encapsulating vilanterol trifenatate.

Figure 2:
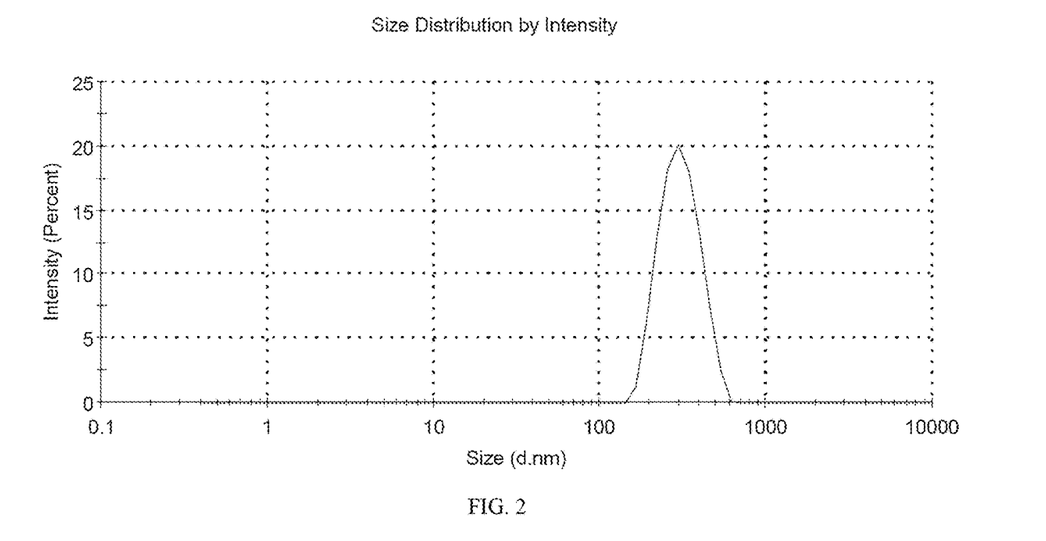
FIG. 2 is a graph of the size distribution of the vilanterol trifenatate liposomes of sample 2 prepared as described in example 2.

Sample 2: NaCl (0.9 g) was added to a beaker containing 100 ml purified water. To this NaCl solution, 117 µL of hydrochloric acid was added. Vilanterol trifenatate (7.03 mg) was added to 70 ml of the solution, then sonicated for 10 min to dissolve. Then, the solution containing vilanterol trifenatate was filtered using a 0.22-µm filter membrane. Then DPPC (44.57 mg), DSPG (5.49 mg), and cholesterol (13.20 mg) were combined in a 50 ml round-bottom flask followed by the addition of 18 ml of chloroform and 2 ml of methanol to dissolve DPPC and DSPG with gentle shaking. The solvent was removed using a rotary evaporator at 65° C., until a thin film of dried lipid was deposited on the walls of the flask. 20 ml of the prepared vilanterol trifenatate solution was added to the round-bottom flask containing the thin layer of dried lipid. The temperature was maintained at 65° C. for approximately 30 minutes. The formulation was then subjected to extrusion using a heated stainless steel extruder assembled with one polycarbonate membrane at 65° C., to reduce the size of the liposomes and improve homogeneity. The extrusion process was repeated for 9-11 passes to achieve 80-200 nm liposomes. After extrusion, NaOH was added to the liposomal solution to adjust the pH to 6.5-7.0. Finally, the liposomal solution was filtered using a 1-μm GF membrane to obtain liposomes encapsulating vilanterol trifenatate.

Figure 3:
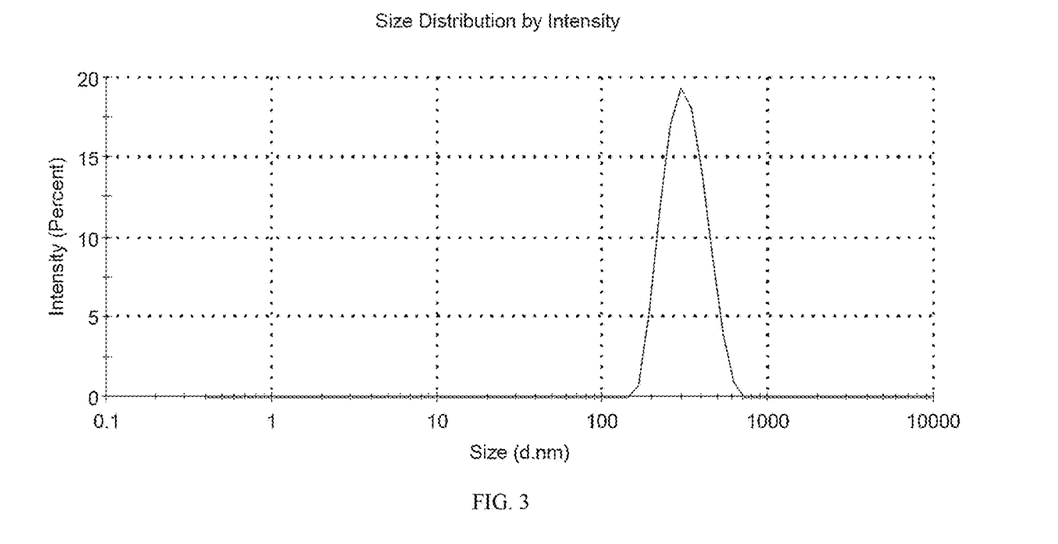
FIG. 3 is a graph of the size distribution of the vilanterol trifenatate liposomes of sample 3 prepared as described in example 2.

Sample 3: NaCl (0.9 g) was added to a beaker containing 100 ml purified water. To this NaCl solution, 117 μL of hydrochloric acid was added. Vilanterol trifenatate (7.03 mg) was added to 70 ml of the solution, then sonicated for 10 min to dissolve. Then, the solution containing vilanterol trifenatate was filtered using a 0.22-μm filter membrane. Then DPPC (27.05 mg), DSPG (3.25 mg), and cholesterol (7.84 mg) were combined in a 50-ml round-bottom flask followed by the addition of 18 ml of chloroform and 2 ml of methanol to dissolve DPPC and DSPG with gentle shaking. The solvent was removed using a rotary evaporator at 65° C., until a thin film of dried lipid was deposited on the walls of the flask. 20 ml of the prepared vilanterol trifenatate solution was added to the round-bottom flask containing the thin layer of dried lipid. The temperature was maintained at 65° C. for approximately 30 minutes. The formulation was then subjected to extrusion using a heated stainless steel extruder assembled with one polycarbonate membrane at 65° C., to reduce the size of the liposomes and improve homogeneity. The extrusion process was repeated for 9-11 passes to achieve 80-200 nm liposomes. After extrusion, NaOH was added to the liposomal solution to adjust the pH to 6.5-7.0. Finally, the liposomal solution was filtered using a 1-μm GF membrane to obtain liposomes encapsulating vilanterol trifenatate.

Figure 4:
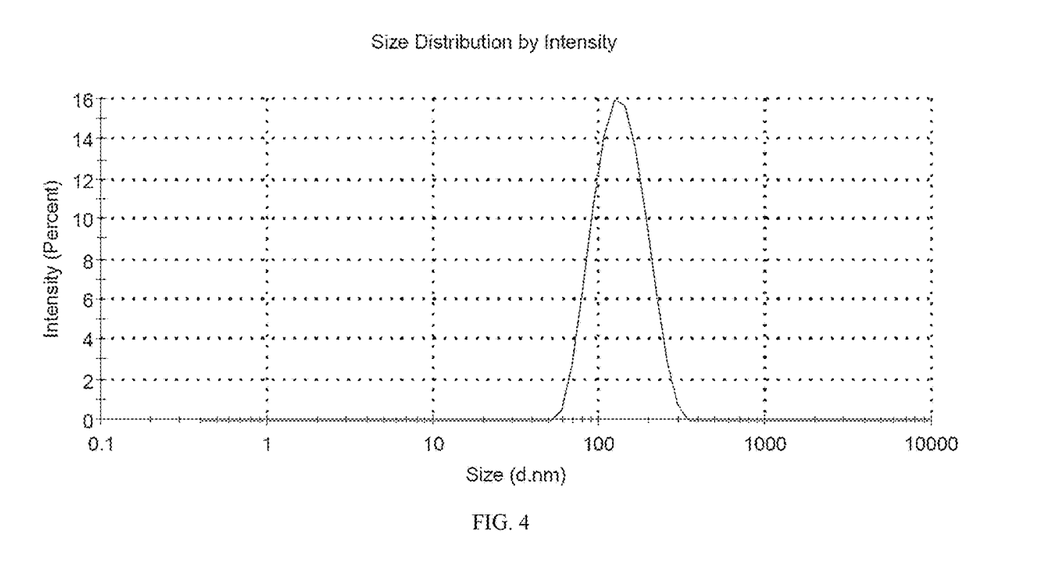
FIG. 4 is a graph of the size distribution of the vilanterol trifenatate liposomes of sample 4 prepared as described in example 2.

Sample 4: NaCl (0.9 g) was added to a beaker containing 100 ml purified water. To this NaCl solution, 117 μL of hydrochloric acid was added. Vilanterol trifenatate (10.4 mg) was added to 70 ml of the solution, then sonicated for 10 min to dissolve. Then, the solution containing vilanterol trifenatate was filtered using a 0.22-μm filter membrane. Then DPPC (44.68 mg), DSPG (5.44 mg), and cholesterol (13.11 mg) were combined in a 50-ml round-bottom flask followed by the addition of 18 ml of chloroform and 2 ml of methanol to dissolve DPPC and DSPG with gentle shaking. The solvent was removed using a rotary evaporator at 65° C., until a thin film of dried lipid was deposited on the walls of the flask. 20 ml of the prepared vilanterol trifenatate solution was added to the round-bottom flask containing the thin layer of dried lipid. The temperature was maintained at 65° C. for approximately 30 minutes. The formulation was then subjected to extrusion using a heated stainless steel extruder assembled with one polycarbonate membrane at 65° C., to reduce the size of the liposomes and improve homogeneity. The extrusion process was repeated for 9-11 passes to achieve 80-200 nm liposomes. After extrusion, NaOH was added to the liposomal solution to adjust the pH to 6.5-7.0. Finally, the liposomal solution was filtered using a 1-μm GF membrane to obtain liposomes encapsulating vilanterol trifenatate.

The particle size of each of the above four samples of liposomal formulation was analyzed using a Malvern Nano ZS90 particle size analyzer.

Example 3

All four samples prepared in above example 2 were evaluated for drug-loading using HPLC, and the particle size was measured using a Malvern Nano ZS90 particle size analyzer. As shown in table 1, the encapsulation efficiency of each of the four samples was above 95%. Furthermore, the average particle size recorded was in the range of about 120 nm to about 320 nm.

TABLE 1

Parameter list of the samples

| Parameter | Sample 1 | Sample 2 | Sample 3 | Sample 4 |
|---|---|---|---|---|
| Drug to lipid ratio | 1:100 | 1:50 | 1:30 | 1:50 |
| Drug-loading (μg/ml) | 100.18 | 86.58 | 105.72 | 110.28 |
| Average particle size (nm) | 261.6 | 286.07 | 311.23 | 125.27 |
| Encapsulation efficiency (%) | 97.67 | 100 | 98.21 | 100 |

Example 4

The drug release profile of sample 2, as described in example 2, was studied by taking 10 ml of the liposomal formulation and loading it into a dialysis bag. The dialysis bag containing the liposomal formulation was kept in 400 ml PBS solution and stirred. The dialysate (PBS solution) was taken every half hour to measure the vilanterol trifenatate content. The results are tabulated in Table 2.

TABLE 2

Drug release profile of drug-loaded liposome

| | Time (h) | | | | | | |
|---|---|---|---|---|---|---|---|
| | 0.5 | 1 | 2 | 3 | 4 | 6 | 24 |
| Cumulative Release (%) | 19.54 | 35.16 | 50.59 | 62.74 | 74.62 | 82.98 | 97.90 |

Example 5

Preparation Method 2:

Preparation of drug solution: NaCl (0.9 g) and 100 ml of purified water were combined in a beaker. The pH was adjusted using 1174, of hydrochloric acid solution. Vilanterol trifenatate (10.04 mg) was added to 80 ml of the solution, then sonicated for 10 min to dissolve. The solution containing vilanterol trifenatate was filtered using a 0.22-μm MCE membrane.

Injecting lipid solution into the drug solution: 29.91 mg of DPPC and 15.61 mg of cholesterol were combined in a beaker containing 15 ml ethanol, and then the beaker was placed in a water bath at 50° C. to fully dissolve. 30 mL of the vilanterol trifenatate solution prepared above was added to a beaker and stirred continuously. The prepared lipid solution was injected into the vilanterol trifenatate solution in the beaker. After the addition of the lipid solution, the resulting solution was stirred for at least 20 minutes.

pH adjustment: Following stirring, the resulting solution was transferred to a 50-ml volumetric flask, and the pH was adjusted to 2.0. Finally, the volume was adjusted to 50 ml using purified water.

Example 6

Figure 5:
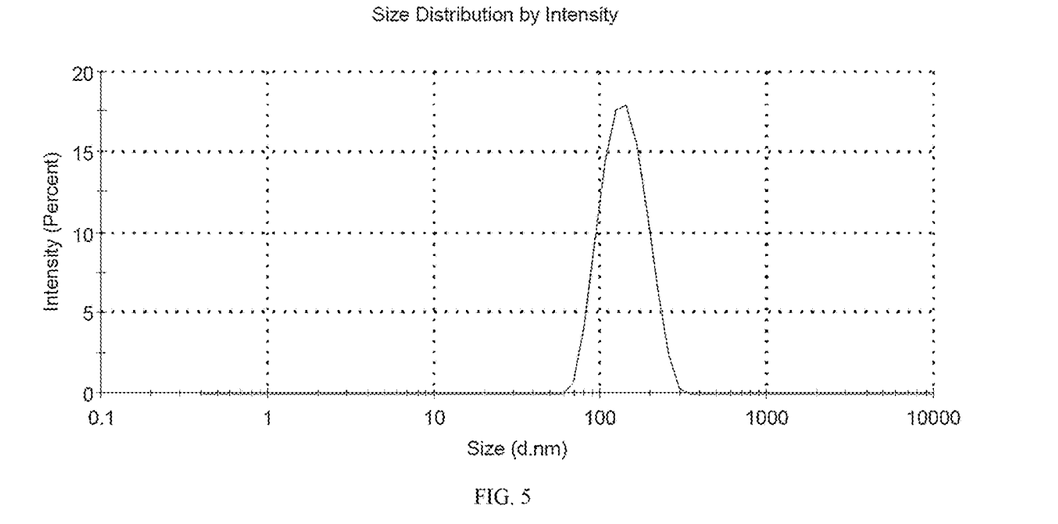
FIG. 5 is a graph of the size distribution of the vilanterol trifenatate liposomes of sample 5 prepared as described in example 6.
Figure 6:
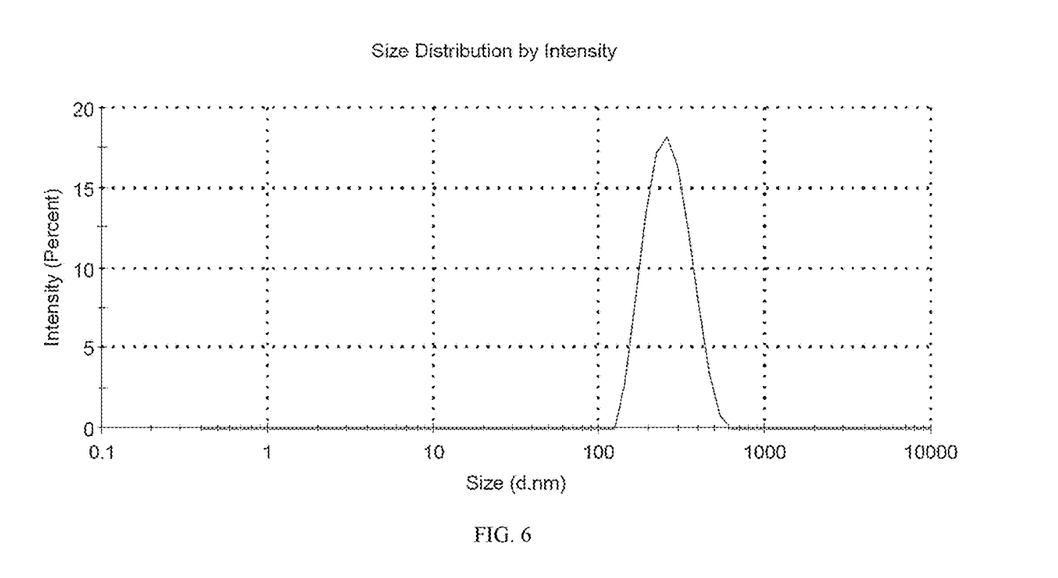
FIG. 6 is a graph of the size distribution of the vilanterol trifenatate liposomes of sample 6 prepared as described in example 6.
Figure 7:
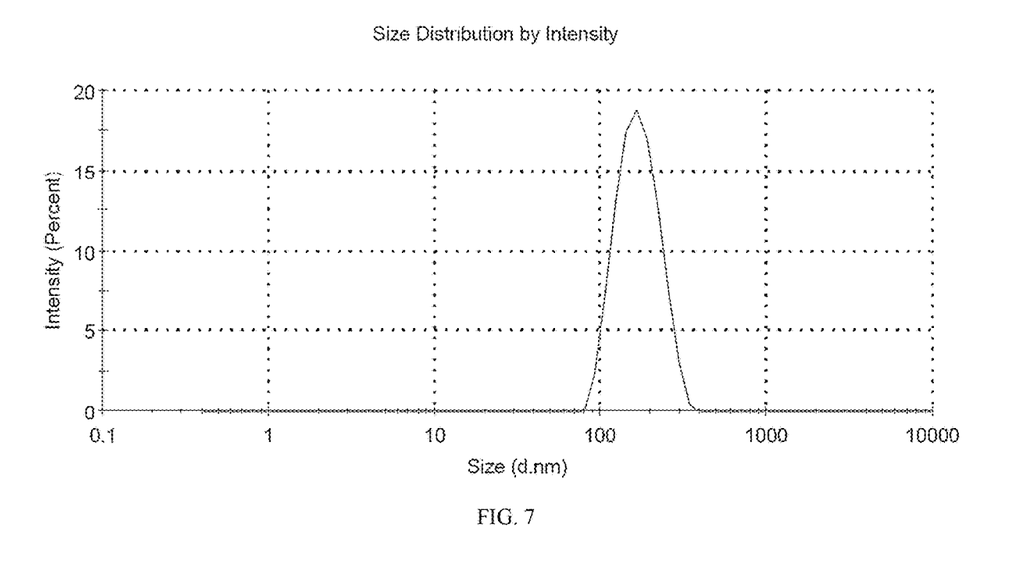
FIG. 7 is a graph of the size distribution of the vilanterol trifenatate liposomes of sample 7 prepared as described in example 6.
Figure 8:
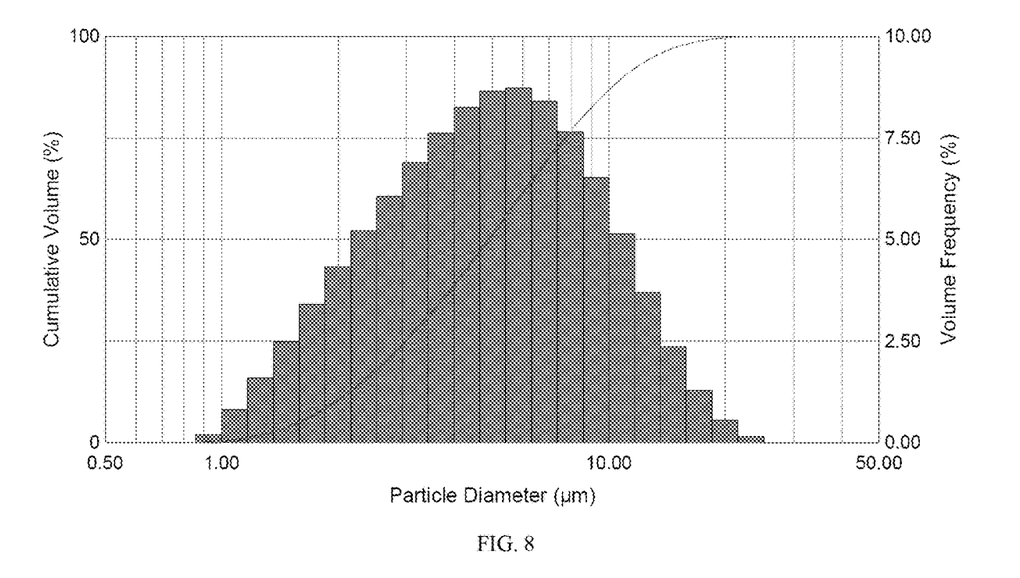
FIG. 8 is a graph of the particle size distribution of droplets of sample 1 formed with a compressed air nebulizer.
Figure 9:
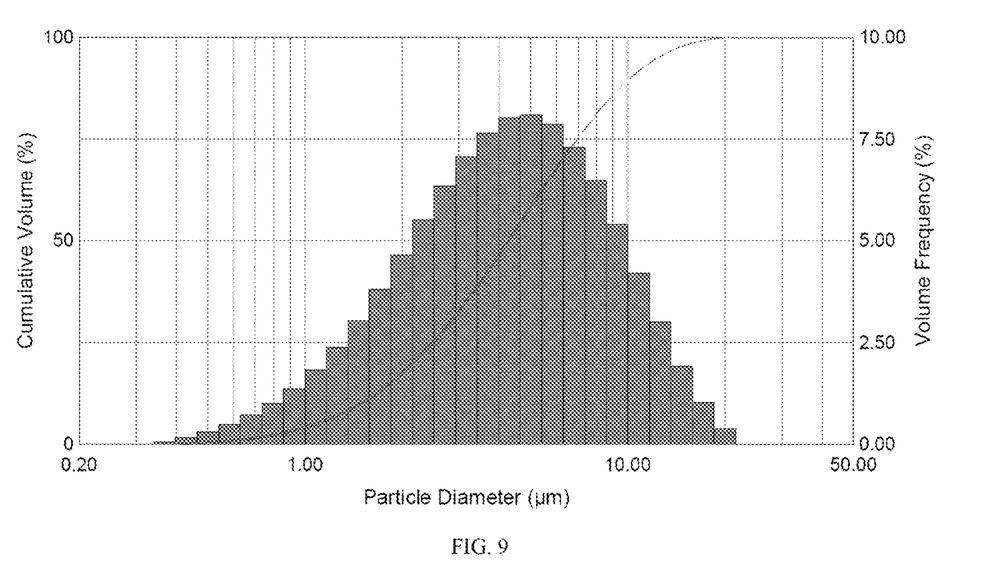
FIG. 9 is a graph of the particle size distribution of droplets of sample 2 formed with a compressed air nebulizer.
Figure 10:
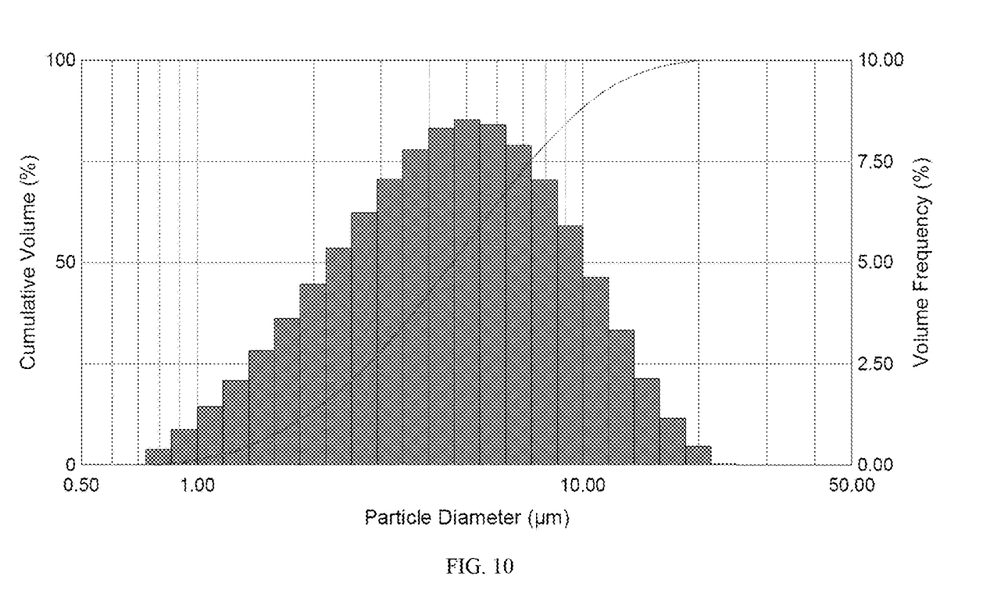
FIG. 10 is a graph of the particle size distribution of droplets of sample 3 formed with a compressed air nebulizer.
Figure 11:
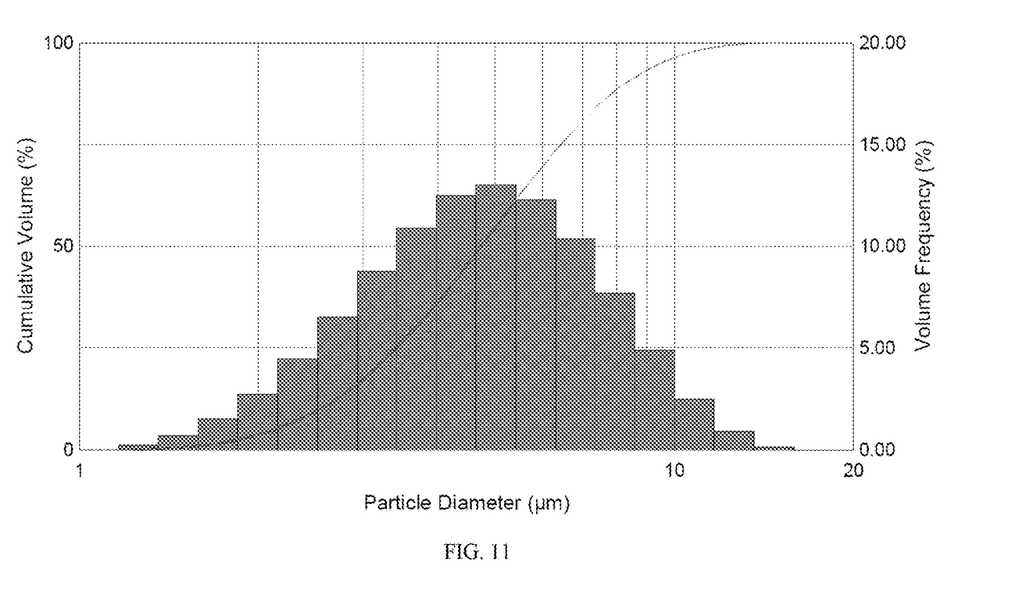
FIG. 11 is a graph of the particle size distribution of droplets of sample 1 formed with an ultrasonic vibrating mesh nebulizer.
Figure 12:
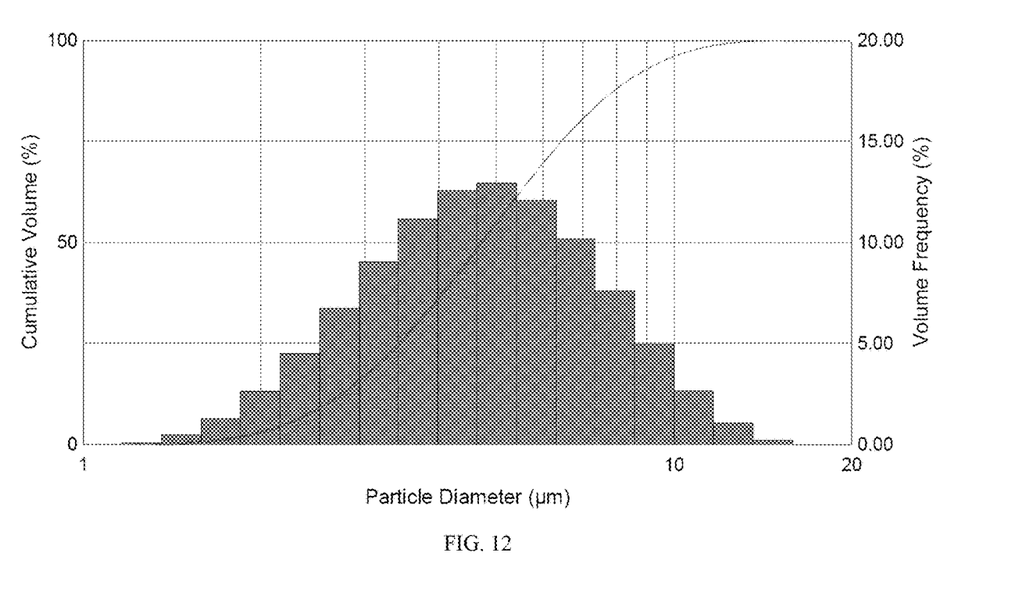
FIG. 12 is a graph of the particle size distribution of droplets of sample 2 formed with an ultrasonic vibrating mesh nebulizer.
Figure 13:
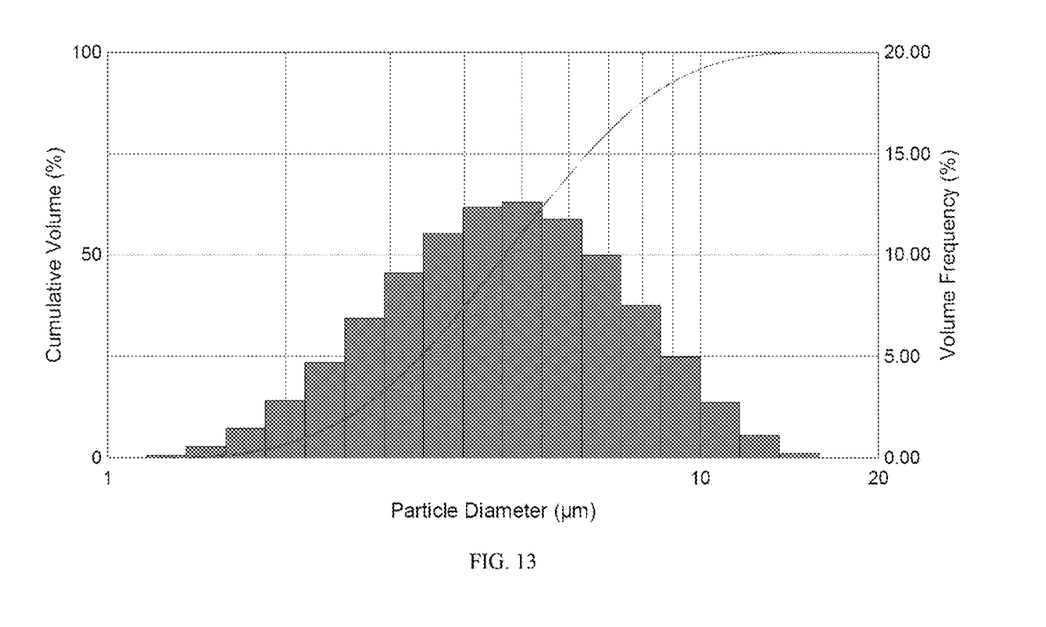
FIG. 13 is a graph of the particle size distribution of droplets of sample 3 formed with an ultrasonic vibrating mesh nebulizer.
Figure 14:
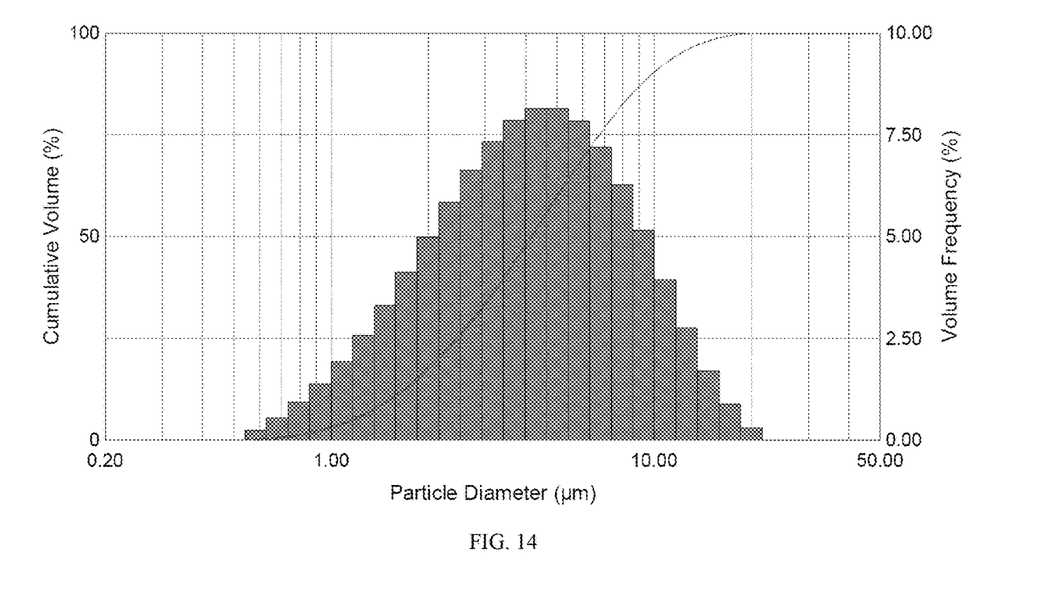
FIG. 14 is a graph of the particle size distribution of droplets of sample 5 formed with a compressed air nebulizer.
Figure 15:
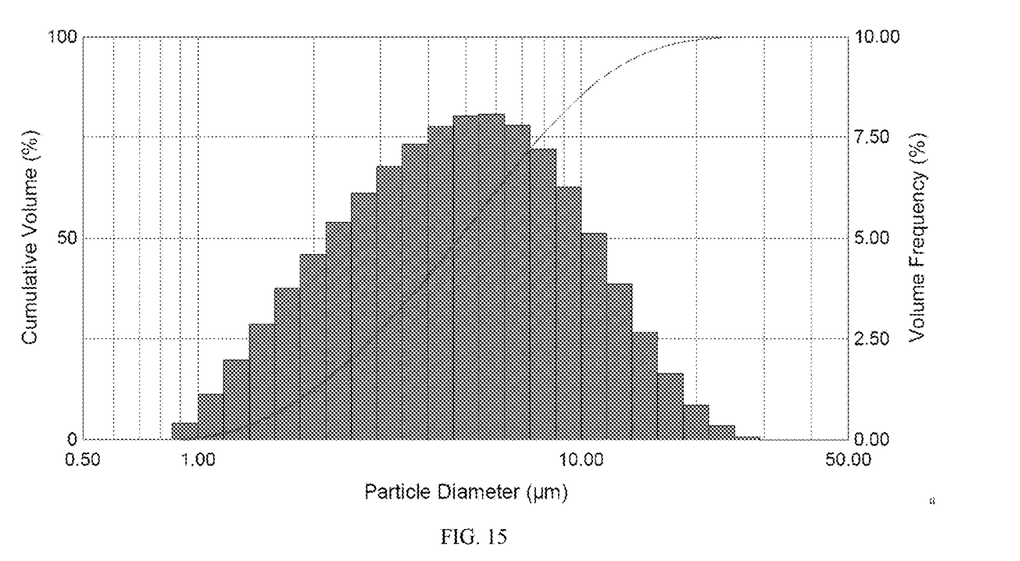
FIG. 15 is a graph of the particle size distribution of droplets of sample 6 formed with a compressed air nebulizer.
Figure 16:
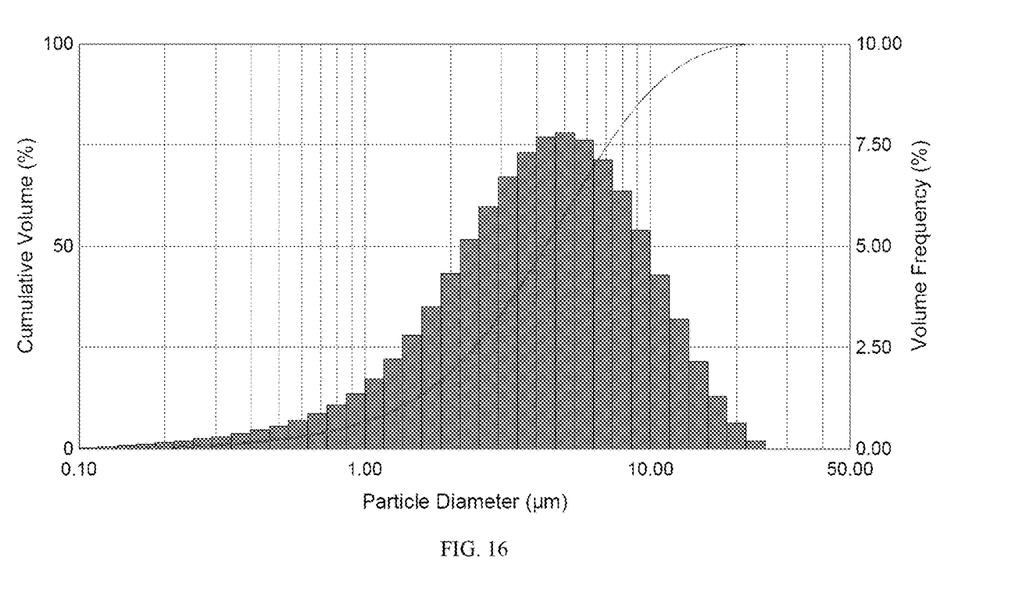
FIG. 16 is a graph of the particle size distribution of droplets of sample 7 formed with a compressed air nebulizer.
Figure 17:
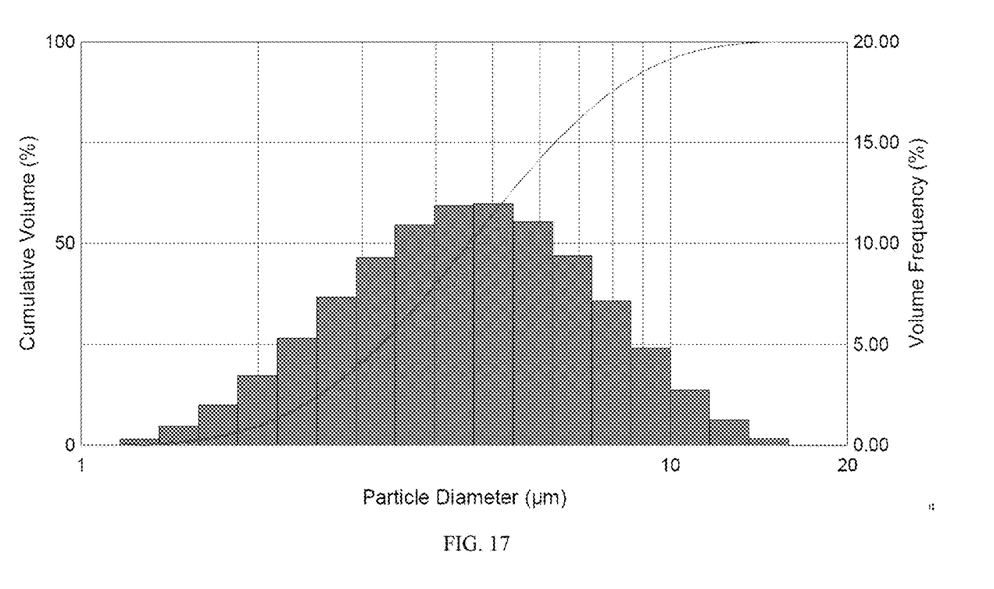
FIG. 17 is a graph of the particle size distribution of droplets of sample 5 formed with an ultrasonic vibrating mesh nebulizer.
Figure 18:
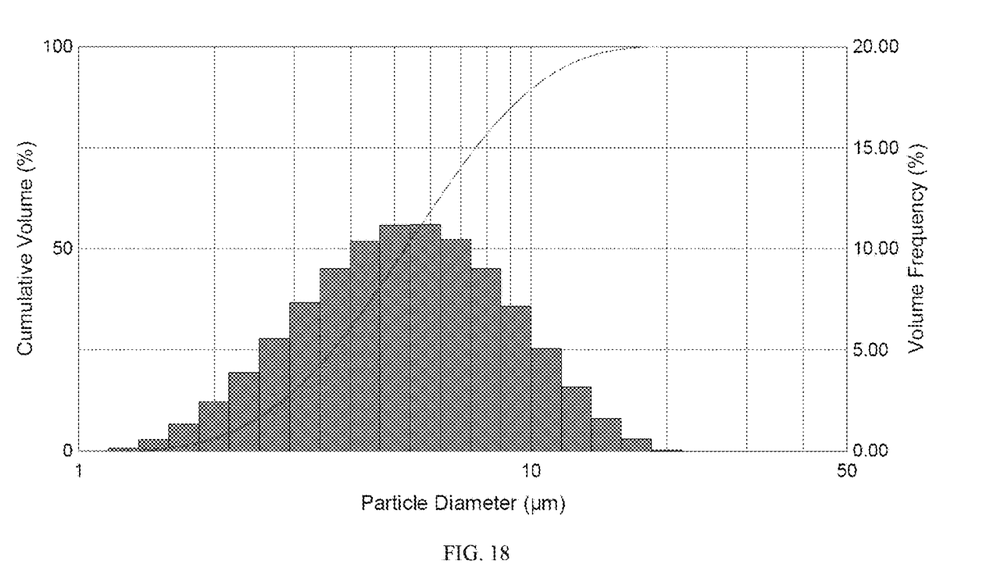
FIG. 18 is a graph of the particle size distribution of droplets of sample 7 formed with an ultrasonic vibrating mesh nebulizer.

In accordance with the preparation method described in example 5, three different samples were prepared with high encapsulation efficiency and different drug to lipid ratios. The encapsulation efficiency of each of the three samples was over 95%, and the encapsulation efficiency of each of sample 5 and sample 7 was 100%. The average particle sizes of the liposomes were in range of about 120 nm to about 260 nm.

Sample 5: NaCl (0.9 g) and 100 ml of purified water were combined in a beaker. The pH was adjusted using 117 μL of hydrochloric acid solution. Vilanterol trifenatate (10.04 mg) was added to 80 ml of the solution, then sonicated for 10 min to dissolve. The solution containing vilanterol trifenatate was filtered using a 0.22-μm MCE membrane. Then, 29.91 mg DPPC and 15.61 mg cholesterol were dissolved in 15 ml ethanol, which was heated to temperature of 50° C. in a beaker, and mixed until completely dissolved to provide a lipid solution. 30 mL of the vilanterol trifenatate solution prepared above was added to a separate beaker and stirred continuously. The prepared lipid solution was added dropwise to the beaker containing the vilanterol trifenatate solution. After the addition of the lipid solution, the resulting solution was stirred for at least 20 minutes. Following stirring, the resulting solution was transferred to a 50-ml volumetric flask, and the pH was adjusted to 2.0. The volume was adjusted to 50 ml with normal saline.

Sample 6: NaCl (0.9 g) and 100 ml of purified water were combined in a beaker. The pH was adjusted using 117 μL of hydrochloric acid solution. Vilanterol trifenatate (7.03 mg) was added to 80 ml of the solution, then sonicated for 10 min to dissolve. The solution containing vilanterol trifenatate was filtered using a 0.22-μm MCE membrane. Then, 32.6 mg DPPC and 17.62 mg cholesterol were dissolved in 15 ml ethanol, which was heated to temperature of 50° C. in a beaker, and mixed until completely dissolved to provide a lipid solution. 30 mL of the vilanterol trifenatate solution prepared above was added to a separate beaker and stirred continuously. The prepared lipid solution was added dropwise to the beaker containing the vilanterol trifenatate solution. After the addition of the lipid solution, the resulting solution was stirred for at least 20 minutes. Following stirring, the resulting solution was transferred to a 50-ml volumetric flask, and the pH was adjusted to 2.0. The volume was adjusted to 50 ml with normal saline.

Sample 7: NaCl (0.9 g) and 100 ml of purified water were combined in a beaker. The pH was adjusted using 117 μL of hydrochloric acid solution. Vilanterol trifenatate (10.40) was added to 80 ml of the solution, then sonicated for 10 min to dissolve. The solution containing vilanterol trifenatate was filtered using a 0.22-μm MCE membrane. Then, 74.94 mg DPPC and 39.67 mg cholesterol were dissolved in 15 ml ethanol, which was heated to temperature of 50° C. in a beaker, and mixed until completely dissolved to provide a lipid solution. 30 mL of the vilanterol trifenatate solution prepared above was added to a separate beaker and stirred continuously. The prepared lipid solution was added dropwise to the beaker containing the vilanterol trifenatate solution. After the addition of the lipid solution, the resulting solution was stirred for at least 20 minutes. Following stirring, the resulting solution was transferred to a 50-ml volumetric flask, and the pH was adjusted to 2.0. The volume was adjusted to 50 ml with normal saline.

The drug-loading was evaluated using HPLC, and the particle size was measured using a Malvern Nano ZS90 particle size analyzer. As shown in Table 2, the encapsulation efficiency of each of the three samples was above 95%. Furthermore, the average particle size recorded is in the range of 120 nm-250 nm.

TABLE 2

Parameter list of the samples

| Parameter | Sample 5 | Sample 6 | Sample 7 |
|---|---|---|---|
| Drug to lipid ratio | 1:20 | 1:30 | 1:50 |
| Drug-loading (μg/ml) | 24.84 | 29.32 | 20.57 |
| Average particle size (nm) | 132.3 | 247.1 | 160.43 |
| Encapsulation efficiency (%) | 100 | 96 | 100 |

Example 7

Sample 1, sample 2, and sample 3 were sprayed using each of an ultrasonic vibrating mesh nebulizer and a compressed air nebulizer. A Malvern Spraytec (STP5311) particle size analyzer was used to measure the particle size distribution of the resulting droplets. The particle size distribution of the droplets is expressed in terms of D10, D50, and D90. The results are shown in table 3 and table 4. The D50 values of the droplets formed using each of the compressed air nebulizer and the ultrasonic vibrating mesh nebulizer were less than 10 μm, and similarly D90 values of droplets formed using each of the compressed air nebulizer and the ultrasonic vibrating mesh nebulizer are less than 15 μm.

TABLE 3

Particle size distribution using compressed air nebulizer

| Sample Number | Sample 1 | Sample 2 | Sample 3 |
|---|---|---|---|
| Drug to lipid ratio | 1:100 | 1:50 | 1:30 |
| $D_{10}$ | 1.93 | 1.45 | 1.78 |
| $D_{50}$ | 4.85 | 4.34 | 4.71 |
| $D_{90}$ | 10.8 | 10.3 | 10.4 |

TABLE 4

Particle size distribution using ultrasonic vibrating mesh nebulizer

| Sample Number | Sample 1 | Sample 2 | Sample 3 |
|---|---|---|---|
| Drug to lipid ratio | 1:100 | 1:50 | 1:30 |
| $D_{10}$ | 2.49 | 2.60 | 2.59 |
| $D_{50}$ | 4.68 | 4.86 | 4.91 |
| $D_{90}$ | 8.20 | 9.06 | 9.74 |

Example 8

Sample 5, sample 6, and sample 7 were also sprayed using each of an ultrasonic vibrating mesh nebulizer and a compressed air nebulizer. A Malvern Spraytec (STP5311) particle size analyzer was used to measure the particle size distribution of the resulting droplets. The particle size distribution of the droplets is expressed in terms of D10, D50, and D90. As shown in table 5 and table 6, the D50 values of the droplets formed using each of the compressed air nebulizer and the ultrasonic vibrating mesh nebulizer are less than 10 and D90 values of the droplets formed using each of the compressed air nebulizer and ultrasonic vibrating mesh nebulizer were less than 15

TABLE 5

Particle size distribution using compressed air nebulizer

| Sample Number | Sample 5 | Sample 6 | Sample 7 |
|---|---|---|---|
| Drug to lipid ratio | 1:20 | 1:30 | 1:50 |
| $D_{10}$ | 1.55 | 1.77 | 1.26 |
| $D_{50}$ | 4.33 | 4.58 | 4.26 |
| $D_{90}$ | 10.2 | 10.6 | 10.5 |

TABLE 6

| Particle size distribution using ultrasonic vibrating mesh nebulizer | | | |
|---|---|---|---|
| Sample Number | Sample 5 | Sample 6 | Sample 7 |
| Drug to lipid ratio | 1:20 | 1:30 | 1:50 |
| $D_{10}$ | 2.43 | 2.45 | 2.54 |
| $D_{50}$ | 4.64 | 4.77 | 497 |
| $D_{90}$ | 8.51 | 9.52 | 9.97 |

What is claimed is:

1. A formulation comprising a plurality of liposomes, wherein the liposomes comprise a lipid ingredient encapsulating vilanterol trifenatate, the lipid ingredient comprises a lipid and a sterol, and wherein the vilanterol trifenatate and lipid ingredient are present in a mass ratio of between about 1:10 and about 1:150 (vilanterol trifenatate:lipid ingredient).

2. The formulation according to claim 1, wherein the liposomes have an average size of about 50 nm to about 500 nm.

3. The formulation according to claim 1, wherein the lipid is selected from the group consisting of phosphatidylcholine (PC), phosphatidic acid (PA), phosphatidylethanolamine (PE), phosphatidylglycerol (PG), phosphatidylserine (PS), phosphatidylinositol (PI), dimyristoyl phosphatidyl choline (DMPC), distearoylphosphatidyl choline (DSPC), dipalmitoyl phosphatidyl choline (DPPC), dimyristoyl phosphatidyl glycerol (DMPG), distearoylphosphatidyl glycerol (DSPG), dioleoyl phosphatidyl glycerol (DOPG), dipalmitoylphosphatidylglycerol (DPPG), dimyristoyl phosphatidyl serine (DMPS), distearoyl phosphatidyl serine (DSPS), dioleoyl phosphatidyl serine (DOPS), dipalmitoyl phosphatidyl serine (DPPS), dioleoyl phosphatidyl ethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyp-cyclohexane-1-carboxylate (DOPE-mal), dipalmitoyl phosphatidyl ethanolamine (DPPE), dimyristoylphosphoethanolamine (DMPE), distearoyl-phosphatidylethanolamine (DSPE), di stearoylphosphatidylcholine (DSPC), dioleoylphosphatidylcholine (DOPC), dipalmitoylphosphatidylcholine (DPPC), and combinations thereof.

4. The formulation according to claim 1, wherein the sterol is selected from the group consisting of cholesterol, ergosterol, lanosterol, and combinations thereof.

5. The formulation according to claim 1, wherein the liposomes have a D50 value of less than about 10 μm.

6. The formulation according to claim 1, further comprising an antioxidant selected from the group consisting of a water-soluble antioxidant and an oil-soluble antioxidant.

7. The formulation according to claim 1, wherein the lipid ingredient comprises DPPC, DSPG, and cholesterol, in a molar ratio of about 9:1:5 (DPPC:DSPG:cholesterol).

8. The formulation according to claim 1, wherein the lipid ingredient comprises DPPC and cholesterol, in a molar ratio of about 1:5 (DPPC:cholesterol).

9. A method for preparing a liposomal formulation, comprising: (1) preparing a vilanterol trifenatate solution, (2) preparing a lipid solution, (3) mixing the vilanterol trifenatate solution with the lipid solution to provide a mixture, and (4) extruding the mixture.

10. The method according to claim 9, wherein the liposomal formulation has a pH of about 4.0 to about 7.5.

11. The method according to claim 9, wherein the lipid solution comprises a lipid ingredient, and wherein the vilanterol trifenatate and the lipid ingredient are present in a mass ratio that ranges from about 1:10 to about 1:150.

12. The method according to claim 9, wherein the extruding is carried out at a temperature between about 60° C. and about 70° C.

* * * * *